(12) United States Patent
Friedman et al.

(10) Patent No.: US 10,436,744 B2
(45) Date of Patent: Oct. 8, 2019

(54) 2H/1T PHASE CONTACT ENGINEERING FOR HIGH PERFORMANCE TRANSITION METAL DICHALCOGENIDE CHEMICAL VAPOR SENSORS

(71) Applicant: The Government of the United States of America, as represented by the Secretary of the Navy, Arlington, VA (US)

(72) Inventors: Adam L. Friedman, Silver Spring, MD (US); F. Keith Perkins, Alexandria, VA (US); James C. Culbertson, Alexandria, VA (US); Aubrey T. Hanbicki, Washington, DC (US); Paul M. Campbell, Alexandria, VA (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 192 days.

(21) Appl. No.: 15/479,014

(22) Filed: Apr. 4, 2017

(65) Prior Publication Data

US 2017/0299544 A1    Oct. 19, 2017

Related U.S. Application Data

(60) Provisional application No. 62/324,465, filed on Apr. 19, 2016.

(51) Int. Cl.
*G01N 27/414* (2006.01)
*H01L 29/24* (2006.01)
(Continued)

(52) U.S. Cl.
CPC ............ *G01N 27/4141* (2013.01); *G03F 1/20* (2013.01); *H01L 29/24* (2013.01);
(Continued)

(58) Field of Classification Search
CPC .. G01N 27/4141; G01N 33/0057; G03F 1/20; G03F 7/405; H01L 29/24; H01L 29/66969

See application file for complete search history.

(56) References Cited

U.S. PATENT DOCUMENTS

| | | |
|---|---|---|
| 4,996,108 A | 2/1991 | Divigalpitiya |
| 5,342,701 A | 8/1994 | Miremadi |

(Continued)

FOREIGN PATENT DOCUMENTS

WO        2016 A1     1/2016

OTHER PUBLICATIONS

Lv, Ruitao, et al. "Transition metal dichalcogenides and beyond: synthesis, properties, and applications of single-and few-layer nanosheets." Accounts of chemical research 48.1 (2014): 56-64.

(Continued)

*Primary Examiner* — Seahvosh Nikmanesh
(74) *Attorney, Agent, or Firm* — US Naval Research Laboratory; Stephen T. Hunnius

(57) ABSTRACT

A method of making a low dimensional material chemical vapor sensor comprising providing a monolayer of a transition metal dichalcogenide, applying the monolayer to a substrate, applying a PMMA film, defining trenches, and placing the device in a n-butyl lithium (nbl) bath. A low dimensional material chemical vapor sensor comprising a monolayer of a transition metal dichalcogenide, the monolayer applied to a substrate, a region or regions of the transition metal dichalcogenide that have been treated with n-butyl lithium, the region or regions of the transition metal dichalcogenide that have been treated with n-butyl lithium have transitioned from a semiconducting to metallic phase, (Continued)

metal contacts on the region or regions of the transition metal dichalcogenide that have been treated with the n-butyl lithium.

12 Claims, 13 Drawing Sheets

(51) Int. Cl.
    *G03F 7/40*     (2006.01)
    *H01L 29/66*     (2006.01)
    *G03F 1/20*     (2012.01)
    *G01N 33/00*     (2006.01)

(52) U.S. Cl.
    CPC .... *H01L 29/66969* (2013.01); *G01N 33/0057* (2013.01); *G03F 7/405* (2013.01)

(56) References Cited

U.S. PATENT DOCUMENTS

| | | |
|---|---|---|
| 9,063,063 B2 | 6/2015 | Friedman |
| 9,806,164 B1* | 10/2017 | Terrones ........... H01L 21/02485 |
| 2014/0273259 A1 | 9/2014 | Friedman |
| 2015/0294875 A1* | 10/2015 | Khondaker et al. ... G01N 27/02 436/112 |
| 2018/0024085 A1* | 1/2018 | Friedman ............... G01N 21/77 204/431 |
| 2018/0315852 A1* | 11/2018 | Ozkan ................. H01L 51/0558 |

OTHER PUBLICATIONS

McCreary, Kathleen M., et al. "The effect of preparation conditions on Raman and Photoluminescence of Monolayer WS2." Scientific reports 6 (2016).
Liu, Bilu, et al. "High-performance chemical sensing using Schottky-contacted chemical vapor deposition grown monolayer MoS2 transistors." ACS nano 8.5 (2014): 5304-5314.
Voiry, Damien, Aditya Mohite, and Manish Chhowalla. "Phase engineering of transition metal dichalcogenides." Chemical Society Reviews 44.9 (2015): 2702-2712.
Ma, Yuqiang, et al. "Reversible semiconducting-to-metallic phase transition in chemical vapor deposition grown monolayer WSe2 and applications for devices." ACS nano 9.7 (2015): 7383-7391.

* cited by examiner

2H/1T PHASE CONTACT ENGINEERING FOR HIGH PERFORMANCE TRANSITION METAL DICHALCOGENIDE CHEMICAL VAPOR SENSORS

CROSS-REFERENCE TO RELATED APPLICATIONS

This application claims priority to and the benefits of United States Patent Application Number and claiming priority to U.S. Patent Application No. 62/324,465 filed on Apr. 19, 2016, the entirety of which is herein incorporated by reference.

BACKGROUND

Devices made from single-layer transition metal dichalcogenides (TMDs) offer the promise of inexpensive, flexible, high-performance electronics that exploit their unique monolayer and surface-dominated geometry. Abbreviated chemically as $MX_2$, where M is a transition metal (Mo, W, Nb, etc.) and X is a chalcogen (S, Se, or Te), the TMDs behave as insulators, semiconductors, metals, magnets, and superconductors with a variety of properties distinct from bulk. For instance, the semiconductors $MoX_2$ and $WX_2$ transition from indirect gap semiconductors in the bulk to direct gap as monolayers.

Chemical vapor sensing with monolayers is a particularly promising field, as their inherent few-atom thinness results in extreme sensitivity to surface perturbations. $MoS_2$ is an extraordinarily sensitive chemical vapor sensor, responding selectively to strong electron donors (e.g. amines) through a physisorption process.

A minute quantity of analyte on the surface of the $MoS_2$ acts as an electron donor and local reducing agent, measurably affecting the conductance of the channel. Analytes relevant to identifying explosives and nerve agents have been detected to concentrations as low as 10-50 parts per billion (ppb) by monitoring the conductance of a simple $MoS_2$ field effect transistor (FET). Such sensitivity is comparable to the current state-of-the-art conductance, surface acoustic wave (SAW), and optical chemical vapor sensors.

TMD sensors are also flexible, inexpensive, robust, and require only nanoamperes for operation, making them intrinsically ultra-low power, distinct advantages over other types of sensors.

As physisorption is strongly dependent on the band structure of the material, a variety of TMDs can be combined into a single sensing suite to identify compounds of interest, analyze mixtures, and add sensitivity to the devices, building in essence a synthetic nose.

Most TMD devices used Au only or Ti/Au as the contact metal, which resulted in electronic behavior that is entirely dominated by Schottky contacts. For chemical vapor sensing in particular, poor contacts strongly limit the current in the channel and produce uncontrollable and variable sensitivity to polar molecules. Some suggest that a low work-function material, such as Sc, or a tunable work function material, such as graphene, can provide better contacts. However, Sc only lowers the Schottky barrier without completely eliminating it, and using graphene adds an additional level of complexity to the devices. To achieve the highest functionality, it is suggested that the contacts be Ohmic and not Schottky-limited.

BRIEF SUMMARY OF THE INVENTION

This invention discloses 2H/1T phase contact engineering for high performance transition metal dichalcogenide (TMDs) chemical vapor sensors.

This invention demonstrates that by selectively transitioning the contacts in a transition metal dichalcogenide field effect transistor (FET)-based chemical vapor sensor device, enhanced chemical vapor sensing metrics are established.

These enhancements include: (1) Ohmic contacts leading to behavior no longer dominated by Schottky effects, (2) complete spontaneous recovery of the sensor after chemical exposure, (3) the removal of band-bending effects at the contacts, which lead to an undesired environmentally variable response to polar molecules, and (4) selectivity to labile nitrogen containing electron donor analyte species.

Furthermore, this invention describes a process of creating these phase engineered contacts in monolayer and few-layer $MoS_2$ that can be further applied to any of the semiconducting transition metal dichalcogenide thin films, thus creating a range of chemical vapor sensors that are mechanically robust and flexible, selective, highly sensitive, and yet inexpensive.

The semiconductor-to-metal transition in TMDs offers a pathway toward better chemical selectivity and sensitivity in chemical vapor sensor FET devices by introducing the possibility of selective Ohmic contact engineering. The semiconductor-to-metal transition occurs through compensation for excess strain or charge in the TMD lattice. TMDs naturally prefer the 2H trigonal prismatic formation, where a single monolayer (comprising sequentially stacked chalcogen/transition metal/chalcogen layers) is stacked in an A-B-A sequence. Strain or excess charge forces the material first into an intermediate 1T' state and then into the 1T octahedral state. Here, the atoms are stacked as C-B-A in a stable local energy minimum. This is illustrated in a simple cartoon monolayer cross-section in the insets of FIG. 1A and FIG. 1B. The 2H and 1T phases are differentiated both by conductance measurements, with the metallic phase offering a resistance that is at least an order of magnitude lower, and optical characterization.

DETAILED DESCRIPTION

This invention discloses 2H/1T phase contact engineering for high performance transition metal dichalcogenide (TMDs) chemical vapor sensors.

This invention demonstrates that by selectively transitioning the contacts in a transition metal dichalcogenide field effect transistor (FET)-based chemical vapor sensor device, enhanced chemical vapor sensing metrics are established.

These enhancements include: (1) Ohmic contacts leading to behavior no longer dominated by Schottky effects, (2) complete spontaneous recovery of the sensor after chemical exposure, (3) the removal of band-bending effects at the contacts, which lead to an undesired environmentally variable response to polar molecules, and (4) selectivity to labile nitrogen containing electron donor analyte species.

Example 1

Devices are fabricated from $MoS_2$ flakes that are mechanically exfoliated from a bulk crystal onto 275 nm $SiO_2/n^+$ Si. The $n^+$ Si will act as a back-gate for later electrical measurements. Thin layers are first visually identified with an optical microscope and then confirmed to be monolayer through Raman spectroscopy, shown in FIG. 1A and FIG. 1B, and photoluminescence spectroscopy (PL), shown in line in FIG. 1C. For Raman spectroscopy, the peak-to-peak separation of the $E^1_{2g}$ and $A_{1g}$ modes is associated with the number of layers, with a distance of ~18 cm$^{-1}$ being attributed monolayers and ~21.5 cm$^{-1}$ for bilayers. For PL, because of the direct-to-indirect bandgap transition, a strong emission peak due to the A-exciton dominates for monolayers.

As the number of layers increases, the intensity of the peak decreases rapidly and the position shifts to lower energy because of the drastic change in band structure. After the identification of $MoS_2$ flakes suitable for device processing, we used electron-beam lithography on a PMMA resist layer to define contact regions.

After development, the devices are placed in a 1.6 M n-butyl lithium (nbl) bath overnight in an argon glove box, while the device channel remains masked by PMMA. This serves to transition only the contacts to the 1T phase.

Devices are rinsed in hexanes and deionized water before co-aligned deposition of Ti/Au contacts (5 nm/35 nm) by electron-beam evaporation and lift-off.

Figure 1A:
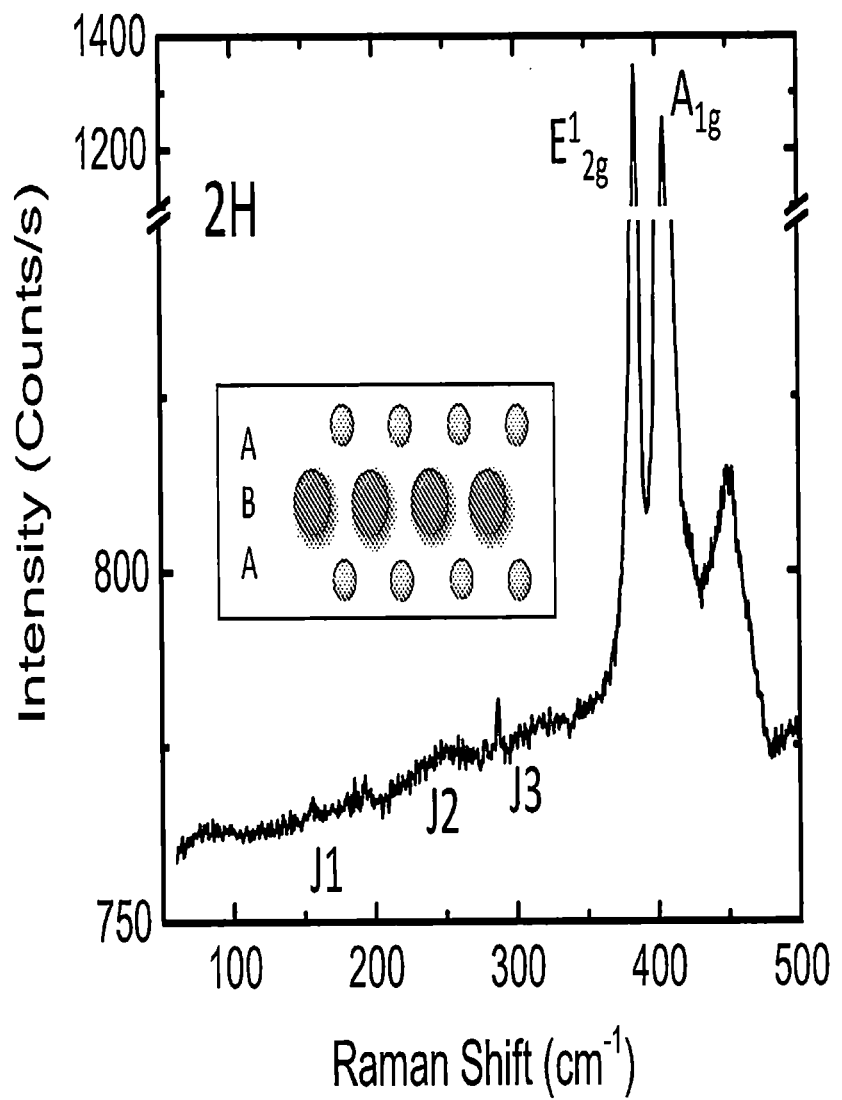
FIG. 1A illustrates Raman spectroscopy spectrum with 488 nm laser showing a $MoS_2$ monolayer film in the 2H state.
Figure 1B:
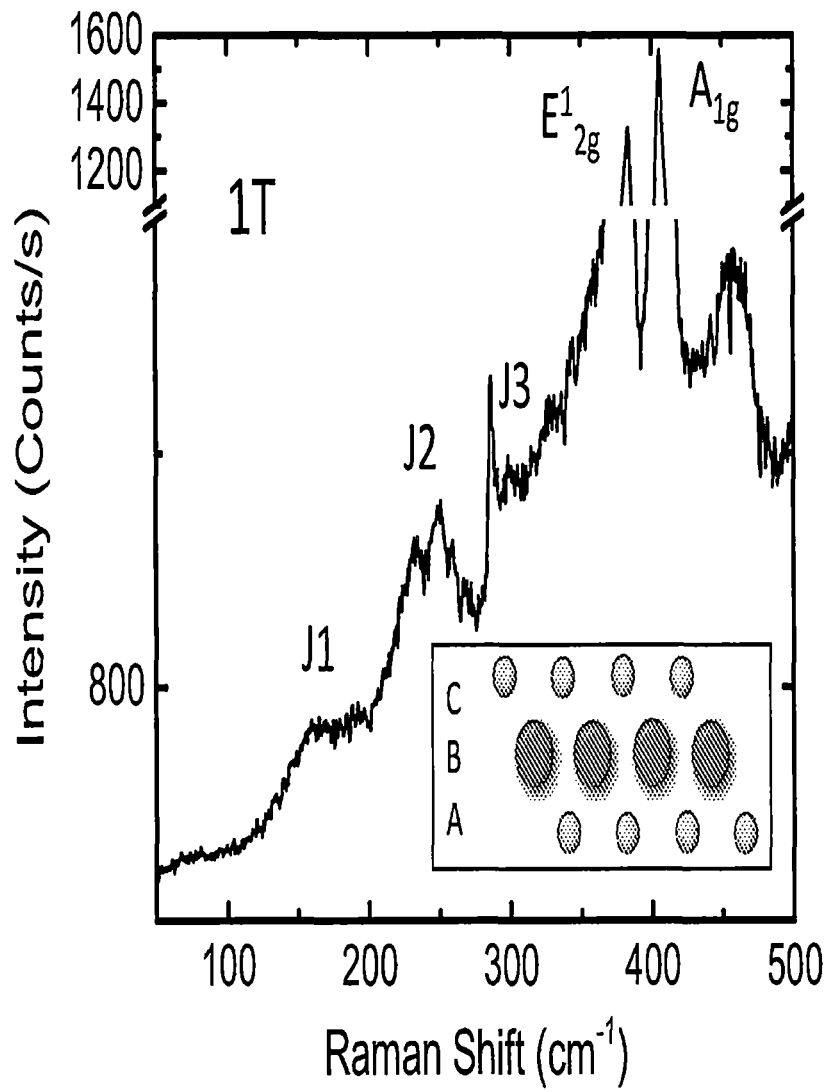
FIG. 1B illustrates Raman spectroscopy spectrum with 488 nm laser showing a $MoS_2$ film in the 1T states after treatment with n-butyl lithium. The emergence of the J1, J2, and J3 peaks indicate a successful transition. The insets in FIG. 1A and FIG. 1B show cartoon schematics of the monolayer 2H and 1T states, respectively.

FIG. 1A and FIG. 1B displays Raman spectra of the 2H (taken before nbl treatment on a witness sample) and 1T (taken after nbl treatment on the same concurrently treated witness sample) $MoS_2$ phases, respectively. The 2H phase has sharp $E^1_{2g}$ and $A_{1g}$ peaks, whereas the J1, J2, and J3 peaks (placed at 156, 226, and 333 cm$^{-1}$, respectively) are difficult to discern from the noise, but hints of them are still visible. After treatment in nbl, the 1T phase $MoS_2$ sample has easily distinguishable J1, J2, and J3 peaks. The intensities of the $E^1_{2g}$ and $A_{1g}$ peaks have not changed significantly, but both have broadened slightly. The sharp peak at ~290 cm$^{-1}$ on both plots is attributed to the $MoS_2$ $E_{1g}$ mode. The enhanced visibility of the J1, J2, and J3 peaks taken together with the broadening of the $E^1_{2g}$ and $A_{1g}$ peaks are firm indicators of 1T phase material.

Figure 1C:
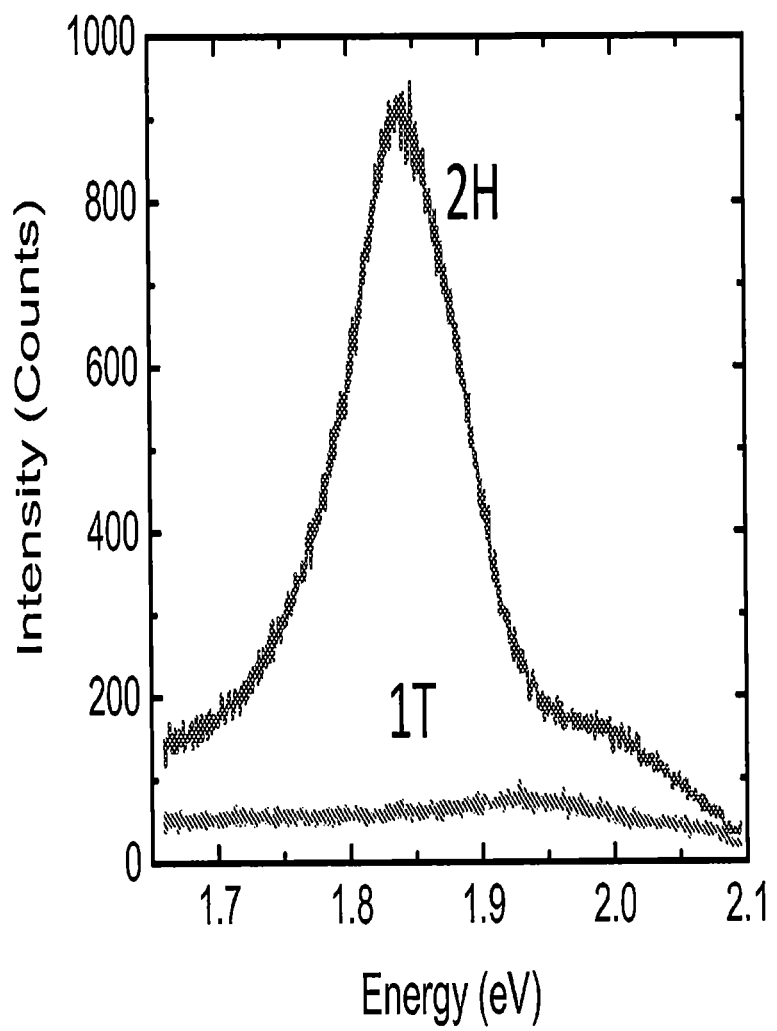
FIG. 1C illustrates photoluminescence spectroscopy of an as exfoliated 2H $MoS_2$ film (blue line) showing strong response indicative of a direct gap semiconductor. The red line shows the same spot on the sample after treatment in n-butyl lithium, showing no photoluminescence, indicating that the film is now in the 1T state.

Further phase identification can be found in the photoluminescence spectra, displayed in FIG. 1C. The 2H phase shows strong luminescence, as described above. After treatment with nbl and transition to the 1T metallic phase, the luminescence disappears as expected. We found that the 2H phase could be recovered by annealing to ~400° C. for test samples with no contacts. Contrary to expectations, annealing experiments on samples with contacts showed that the 2H state could not be recovered. We suspect that this is due to persistent strain provided by the contacts pinning the film to the substrate. Therefore, we can anneal the 1T/2H devices safely without affecting the contact phase configuration.

Figure 1D:
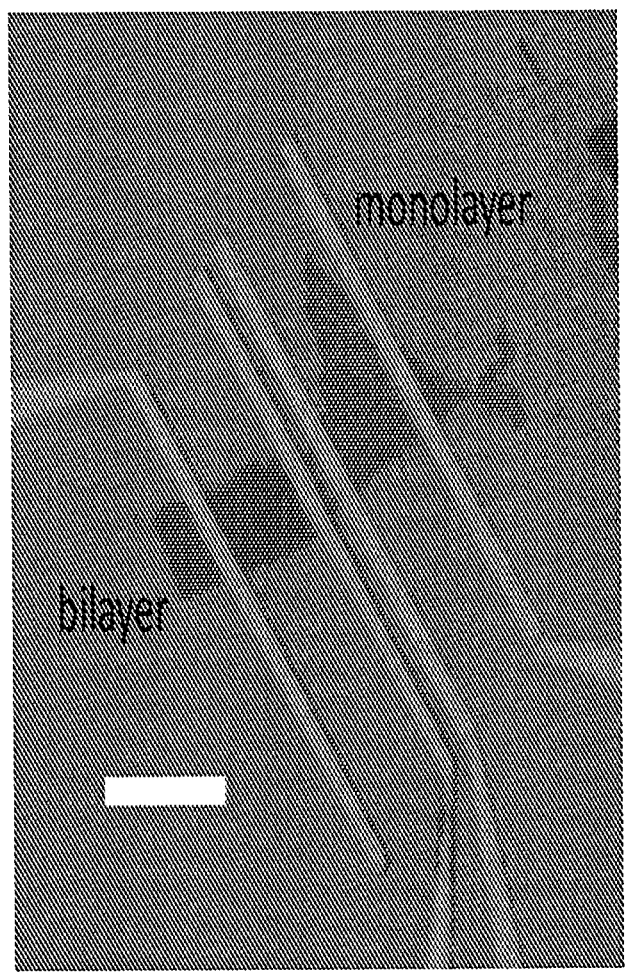
FIG. 1D illustrates optical microscopy image of a typical device used in this study. The right part of the device is a monolayer, the left part of the device is a bilayer. The scale bar is 10 μm.

FIG. 1D displays an optical image of a completed device. This device contains both a monolayer and bilayer sections. For chemical vapor sensing measurements, we did not find significant differences for the monolayer and the bilayer, contrary to previous studies. For chemical vapor sensing measurements, a home-built sensing apparatus was employed.

Example 2

Devices are placed on a sample chuck with heating capabilities for in situ device annealing. Electrical contacts are made with Au-coated W probes, attached to a lock-in amplifier. We apply a small low-frequency AC voltage (100 mV RMS, 2.5 kHz), and the current at that frequency is monitored. A small controlled flow (0-100 sccm) of dry nitrogen is bubbled through liquid analyte to obtain a steady flow of analyte at equilibrium vapor pressure. This is in turn mixed with a larger flow (~5 lpm) of dry nitrogen to obtain a user-controlled concentration of dilute vapor and blown onto the surface of the sample. The analyte vapor stream is directed into and out of the main stream with a computer-controlled solenoid valve.

Figure 2A:
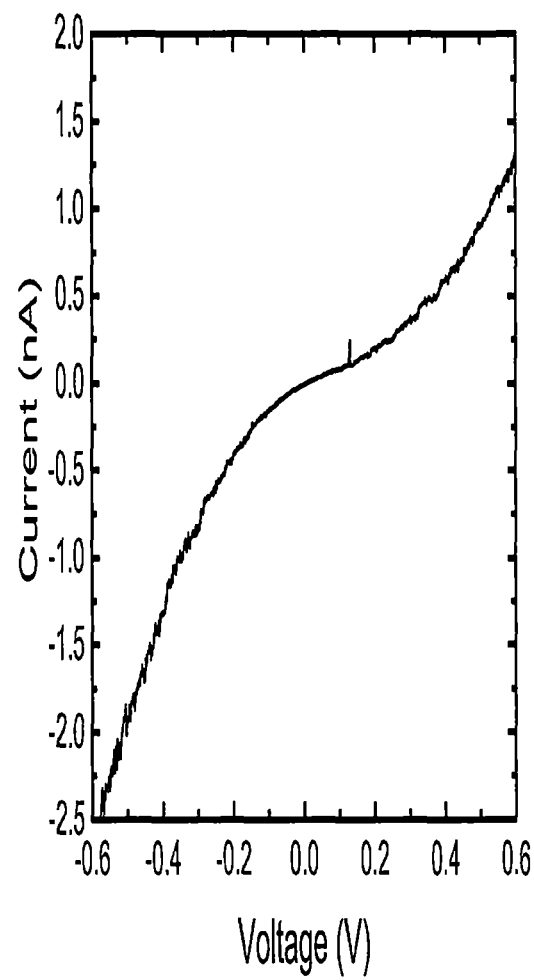
FIG. 2A illustrates IV curve of a device with 2H/2H contacts/channel showing nonlinear, Schottky behavior.
Figure 2B:
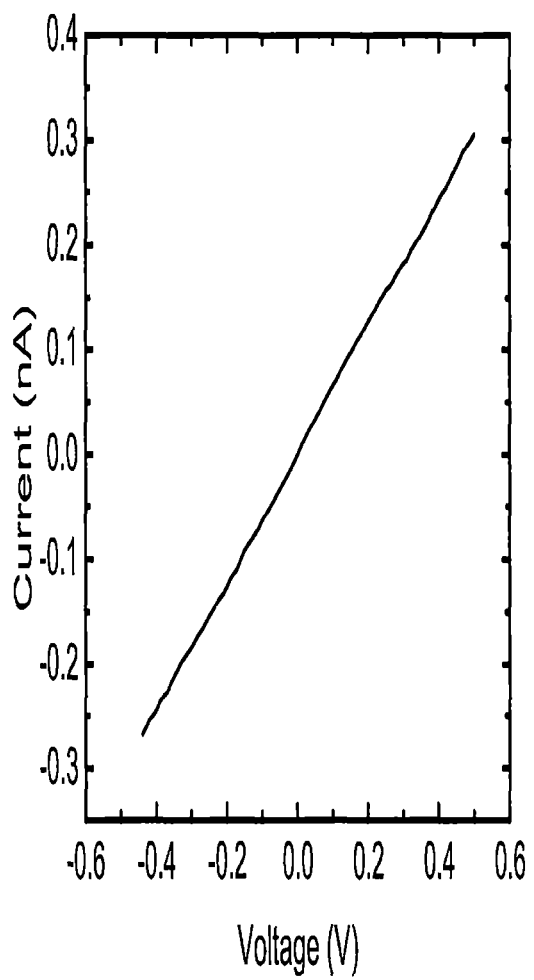
FIG. 2B illustrates IV curve of a device with 1T/2H contacts/channel showing linear, Ohmic behavior.
Figure 2C:
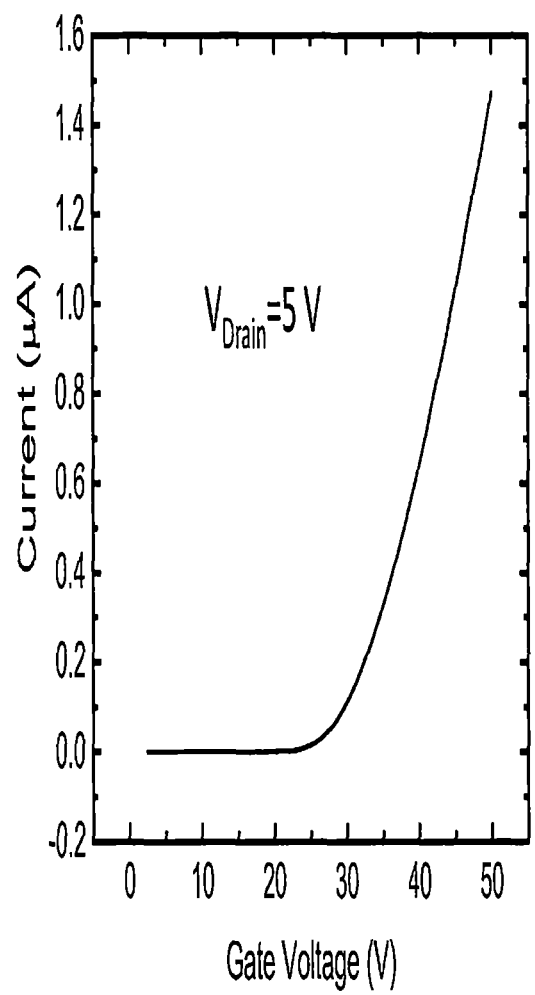
FIG. 2C illustrates gate voltage sweeps for devices with 2H/2H contacts/channel.
Figure 2D:
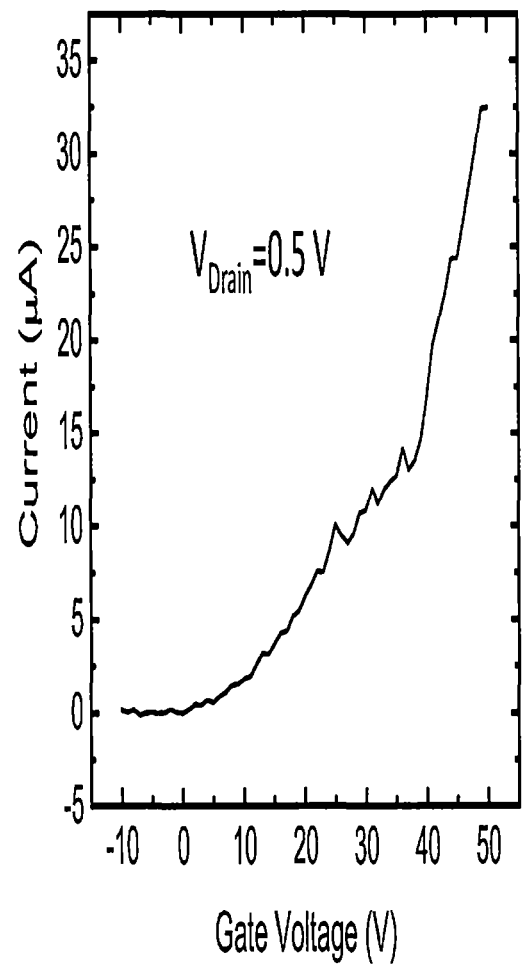
FIG. 2D illustrates gate voltage sweeps for devices with 1T/2H contacts/channel.

FIGS. 2A, 2B, 2C, and 2D compare the room temperature two-terminal electrical characteristics with a gate bias $V_g$=0 of a 2H/2H contact/channel device with a 1T/2H contact/channel device. These measurements were taken on a probe station in ambient. FIG. 2A shows a non-linear IV curve for the 2H/2H device. FIG. 2B shows a linear IV curve for the 1T/2H device, strongly suggestive of the Ohmic behavior reported using the same methods in previous studies. Most devices have $V_g$=0 resistances ranging from 100 MΩ to 10 GΩ. FIG. 2C shows the constant voltage (5V source-drain) back-gate sweep for the 2H/2H device, while FIG. 2D shows the constant voltage (0.5 V source-drain) back-gate sweep for the 1T/2H device. Both devices act as FETs, turning on as the gate voltage is increased. The 2H/2H device has an off-state resistance ~250 MΩ. The resistance begins to fall precipitously at $V_g$~25 V and has a resistance of ~3.3 MΩ at $V_g$=50 V, giving an on/off current ratio of ~$10^2$. The 1T/2H device has an off-state resistance ~1.6 GΩ. The resistance begins to fall precipitously at $V_g$~5 V and has a resistance of ~142 KΩ at $V_g$=50 V, giving an on/off current ratio of ~$10^4$, a large enhancement over the 2H/2H device. While device resistance measured under identical conditions for multiple devices varies by as much as two orders of magnitude, the qualitative behavior was consistent: 2H/2H devices are non-linear and turn on more slowly, while 1T/2H devices are linear and turn on quickly. Therefore, the slightly lower resistance seen in FIG. 2A (2H/2H) as compared to FIG. 2B (1T/2H) is likely an intrinsic property of the 2H $MoS_2$ channel rather than the contacts.

The FET mobility, μ, of the device can be calculated using:

$$\mu = \frac{L}{WC_{ox}V_{Drain}} \frac{\partial I}{\partial V_G}\bigg|_{V=constant}. \quad (1)$$

Here, L and W are the length and width of the channel, $C_{ox}$ is the capacitance per area of the oxide, $V_{Drain}$ is the constant drain voltage. We calculate the slope in the approximately linear portion of the gate voltage curve when the device is fully in the on state. The 2H/2H device has μ~0.16 $cm^2$/Vs and the 1T/2H device has μ~32 $cm^2$/Vs. It is evident that the 1T/2H device has higher FET transconductance and more Ohmic-like contacts than the 2H/2H device. This behavior was consistent for all devices tested.

Example 3

Figure 3A:
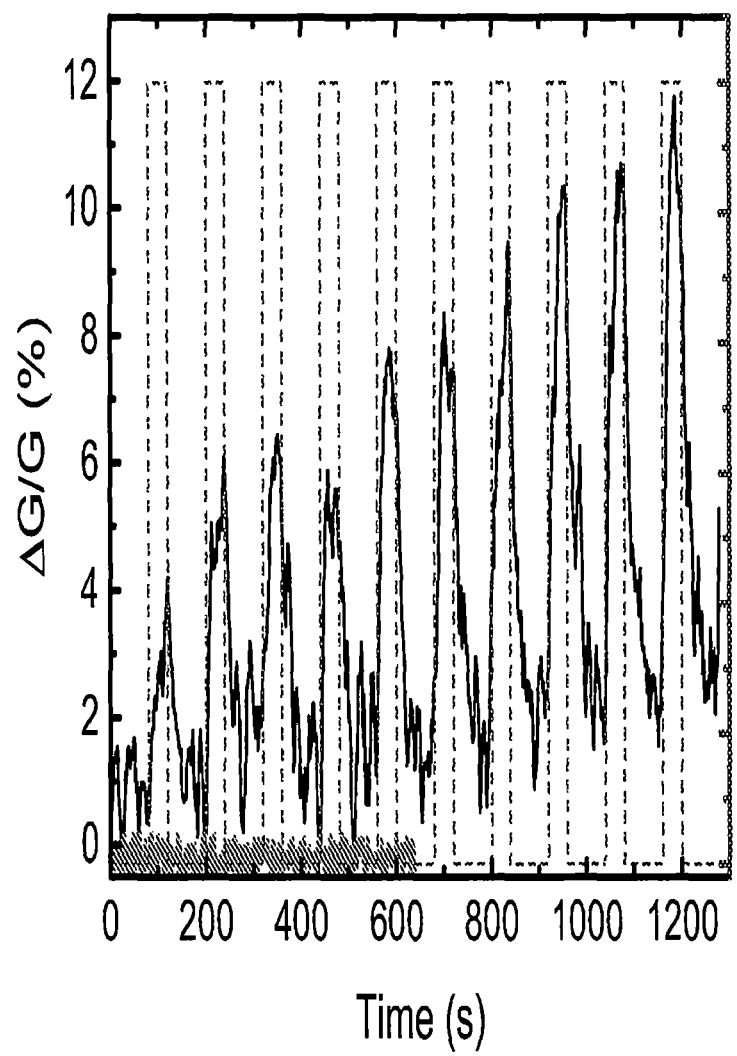
FIG. 3A is a conductance response to a series of 0.06% $P_0$ (~30 ppm) TEA pulses for a 1T/2H contacts/channel $MoS_2$ device (black line).

FIG. 3A displays the 1T/2H sensor response (black line) at $V_g$=0 V to a series of 40 s pulses of triethylamine (TEA) at 0.06% $P_0$ ($P_0$=equilibrium vapor pressure at 22.5° C.), corresponding to ~30 ppm. The dotted line shows the pulse profile. TEA is a strong electron donor and decomposition by-product of VX series nerve agents and amine-based explosives. We see that the conductance is modulated quite quickly in response to the TEA pulse. Moreover, we see that the sensor recovers quickly and almost completely between pulses, unlike the 2H/2H sensor response shown in FIG. 3B as well as in a previous report. For 2H/2H sensors, the Schottky contacts lead to capacitive charge buildup in the device, causing a failure of the device to recover completely. The 1T contact engineering thus results in a significant improvement in device properties. While it can be difficult to determine a minimum sensitivity for the devices due to device-to-device variation and stochastic effects, we extrapolate a minimum sensitivity of ~80 ppb for TEA, which is on order of the minimum we found for the 2H/2H devices previously (10-50 ppb).

Figure 3B:
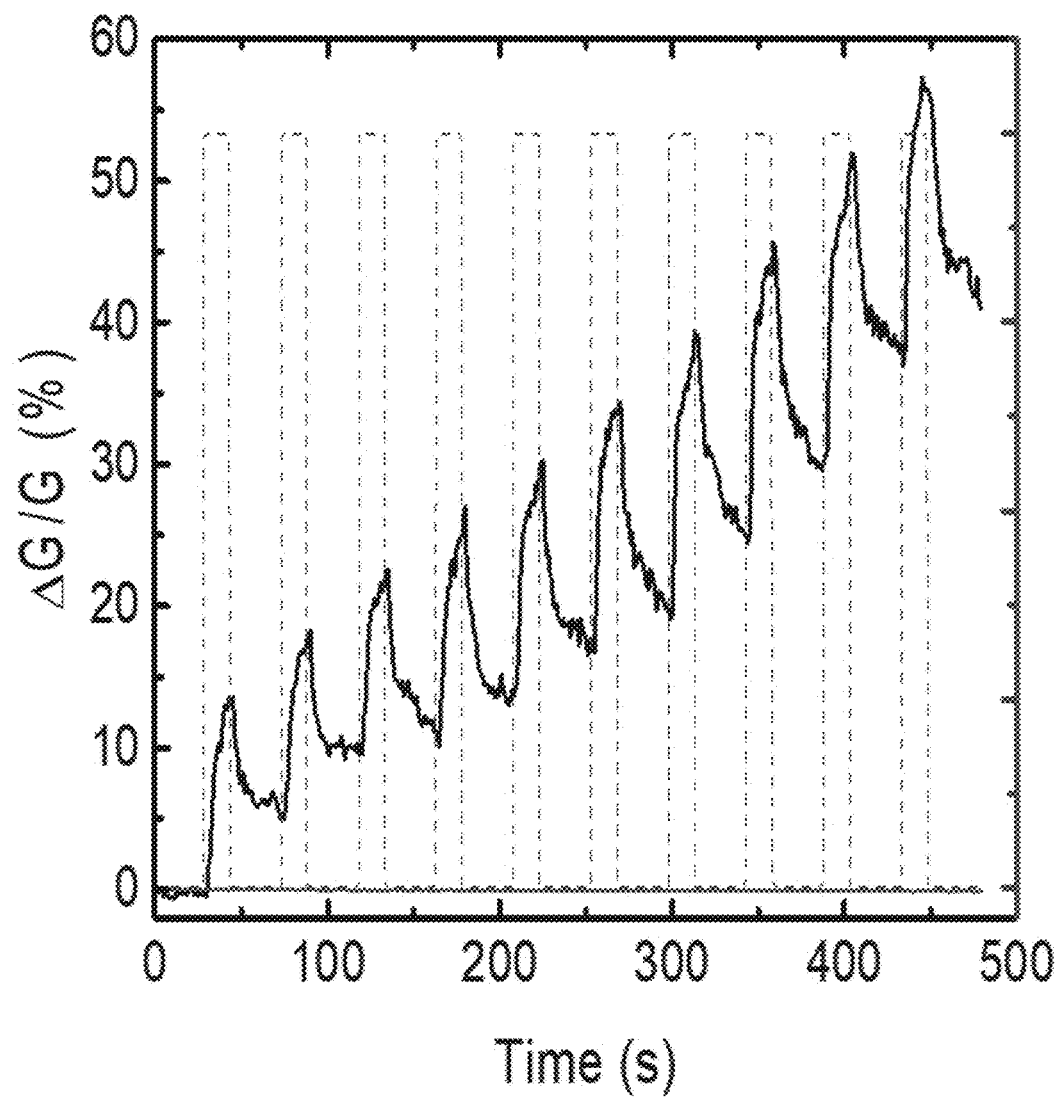
FIG. 3B is a conductance response to a series of 0.02% $P_0$ TEA (~10 ppm) pulses for a 2H/2H contacts/channel $MoS_2$ device (black line). For both FIG. 1A and FIG. 1B, the dotted line shows the pulse profile and the line shows the device response to nitrogen only when the TEA is switched off.

The slight increase in sensor response for each subsequent pulse observed for the 1T/2H device FIG. 3A is interesting, and is also observed for the 2H/2H device in FIG. 3B. The phenomenon is consistent from device to device. However, it appears more pronounced for lower concentrations, which possibly points to a stochastic effect originating in the function of our experimental apparatus, i.e. more analyte physically arrives at the sensor for later pulses than for earlier pulses, as the vapor delivery line takes time to become fully saturated with analyte. Moreover, as the response of the sensor is of much greater magnitude than the noise, and real-world applications will most likely not include pulsing of analyte, it is most likely inconsequential when considering the overall behavior of the sensor.

In previous studies, we noted that the strongest responses were found for highly polar molecules (such as acetone) and strong electron donors (such as TEA), while electron acceptors (such as nitrotoluene) and neutral molecules (i.e., molecules not expected to either donate or accept charge when condensed on the surface, such as alcohols) generated no response whatever. Response to strong electron donors can be explained using a donor-acceptor model, wherein molecules interact weakly with the positively charged sulfur 2p orbitals, as derived through an understanding of $MoS_2$ catalyzed hydrodesulfurization reactions. Moreover, while a significant factor in one-dimensional conductors such as nanotubes, the mobility μ is only weakly affected by adsorbates in these macroscopic films where screening by free carriers can attenuate any scattering effects from adsorbed dipoles. Thus, changes in the carrier concentration n from charge transfer are the only significant means of affecting the device conductivity G=μn through analyte adsorption.

Example 4

Sensing of polar molecules in previous 2H/2H devices was shown to be a purely contact-driven effect, arising from band-bending at the Schottky contacts.

Therefore, for the 1T/2H devices, we expected to see no response to polar molecules. We monitored the conductance of our devices in acetone, methanol, and ethanol vapors and measured no response, further confirming the superiority of the contacts in the 1T/2H sensors.

Example 5

To quantify more fully the selectivity of the sensors, we exposed them to a variety of analytes containing nitrogen, including nitrotoluene (acceptor), aniline (donor), acrylonitrile (donor), nitromethane (acceptor), octylamine (donor), and pyridine (donor). No response was produced after exposure to non-labile nitrogen acrylonitrile, or electron acceptors nitromethane and nitrotoluene. We found a weak response to aniline, and strong responses to both octylamine and pyridine, which exhibited a behavior similar to TEA. The difference in responses to acrylonitrile (for which the nitrogen lone pair is relatively isolated), the labile nitrogen-containing aniline (where the nitrogen lone pair is coplanar and partially conjugated with the π bonds in the aromatic ring), and pyridine (where the nitrogen lone pair is orthogonal to the aromatic π bonds), is significant. Exposures of the devices to non-nitrogen containing species, such as dimethyl methylphosphonate, tetrahydrofuran, or 2-chloroethyl ethyl sulfide produced no response.

We conclude that the $MoS_2$ sensors are selective for strong electron donors with a labile nitrogen atom. Since labile nitrogen-containing species are decomposition by-products of many explosives (most specifically the ammonia-based explosives) and nerve agents (such as VX), these devices are potentially quite useful for identification of these agents in practical sensor in applications.

Example 6

Figure 3C:
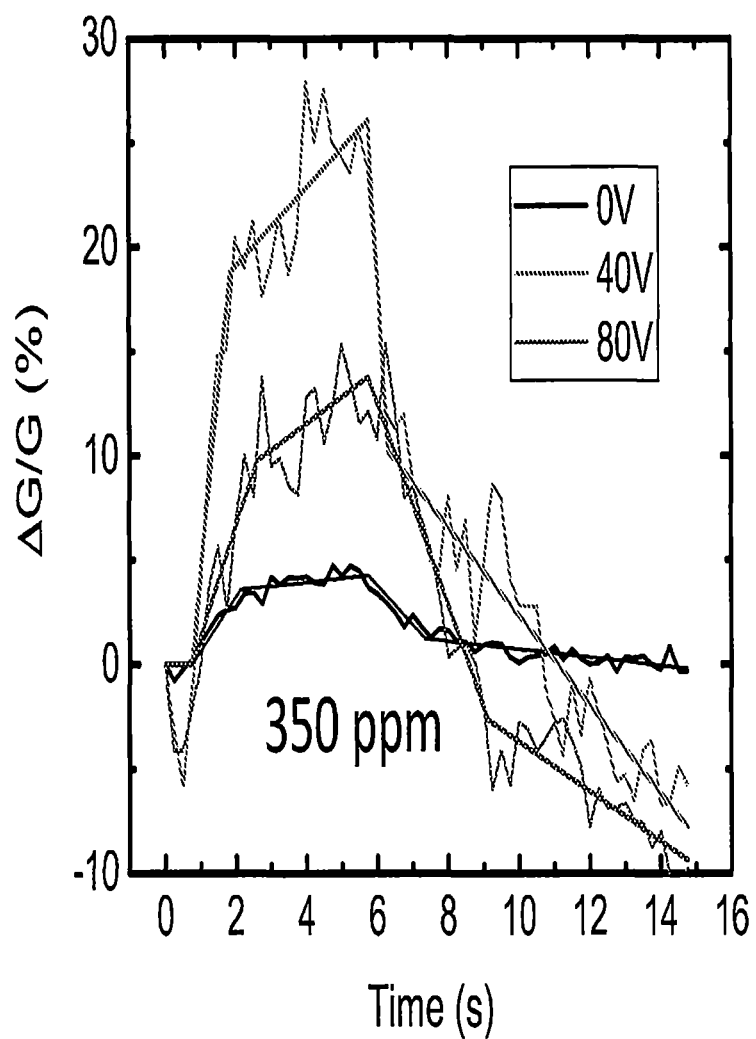
FIG. 3C is a conductance response to a single 6 s 350 ppm TEA vapor pulse as a function of gate voltage for a 1T/2H device.

FIG. 3C shows the response to a single TEA pulse at a variety of gate voltages. The pulse data have been fit to a series of segments to better visualize the pulse response. In our previous 2H/2H devices, and contrary to our expectations, the magnitude of response showed no real dependence on gate voltage, most likely due to the Schottky contact-dominated transport behavior. However, in the 1T/2H devices here, we see an increasing sensitivity for increased gate voltage followed by an eventual decrease in sensitivity. When the gate voltage reaches a level high enough as to cause a large electric field at the surface of the device, it has a repulsive affect on analyte adsorption, leading to a decrease in sensitivity. Alternatively, the increased field along the direction of transport may affect the ability of free carriers to screen the system against charged adsorbates and so allow mobility scattering to become a factor.

Example 7

Figure 4A:
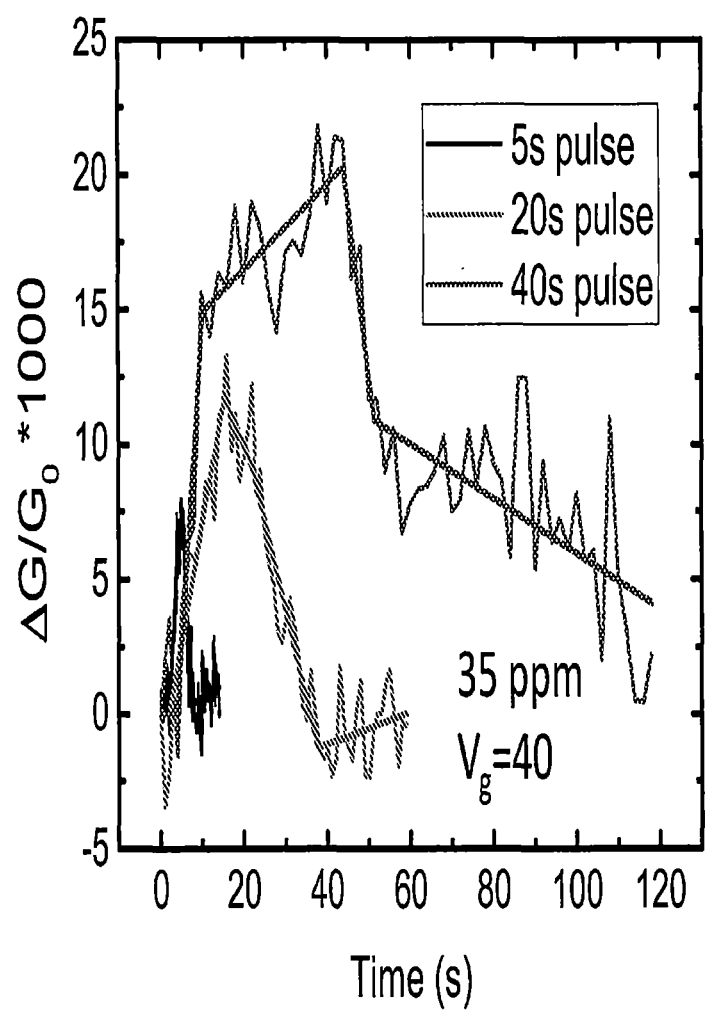
FIG. 4A is a representative pulse response with the portions of the pulse labeled. Here, time t=0 s is assigned to the point where the solenoid valve is switched on, providing analyte vapor to the device under test. The beginning of the response observed at t=0.75 s reflects both the rate of flow from the valve to the sample as well as the time constant of the data acquisition electronics.

To explore the dynamics of the 1T/2H sensor response in more detail, we varied the pulse length for a TEA concentration of 35 ppm (FIG. 4A). We find that the longer the pulse, the longer the recovery period of the device. A longer pulse will result in more accumulation and adsorption of analyte onto the surface of the $MoS_2$ film. This enables kinetically limited processes to permit binding to scarcer, but higher binding energy, sites or molecular orientations. It would then require a longer time for natural, kinetically driven desorption to occur from these energetically deeper sites. It is significant from the standpoint of creating a practical sensor, that devices perform significantly better for shorter pulses.

Figure 4B:
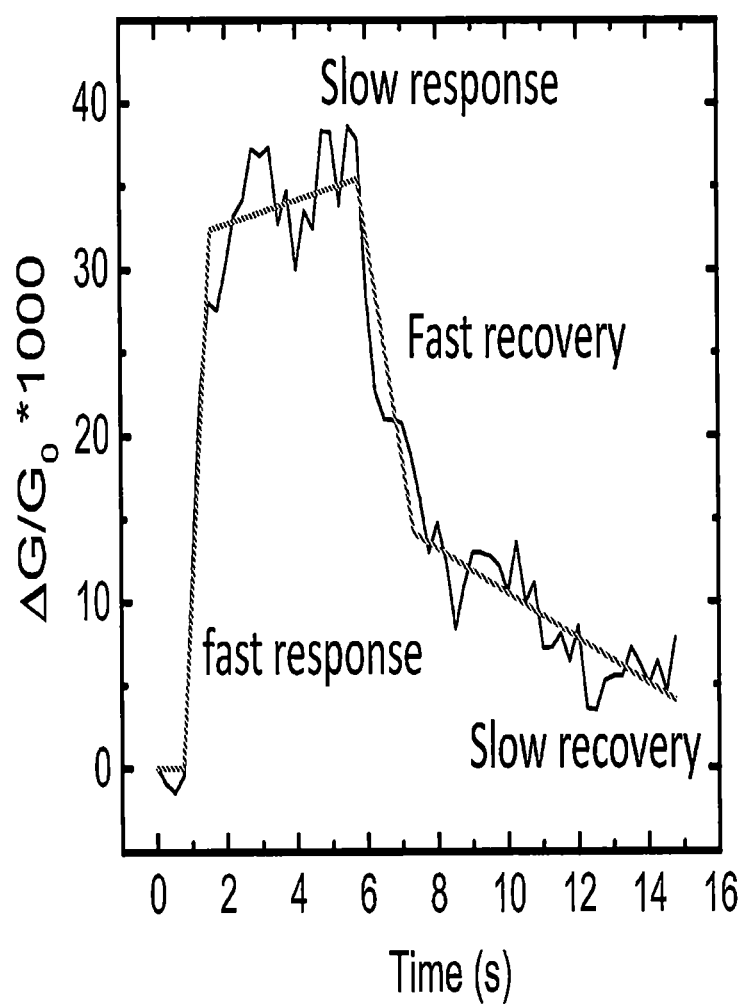
FIG. 4B is a conductance response of a 1T/2H device to 35 ppm TEA, at $V_g$=40 V, with the pulse lengths as indicated.

Referring to the diagram in FIG. 4B, we term the characteristic initial rise in the device the "fast response" and the slower rise thereafter the "slow response." We observe that all responses are initially "fast," and, if the pulse is sufficiently long (on the order of a few seconds), transition abruptly to a subsequent "slow" response. We observe that the slow response does not saturate for 40 s exposures. We attribute the fast response to weak physisorption of molecules onto the "bulk" of the surface, that is, the normal, uniform, un-defected lattice portion of the film. The large size of TEA molecules generally limits the packing density. We attribute the slow response to a different and somewhat stronger interaction, probably at point defects and edges, which are intrinsic to exfoliated layers, but less abundant than for vapor-phase grown films.

Also referring to FIG. 4B, there are two parts to the recovery portion of the response, initiated when the analyte vapor is removed from the ambient stream. The first we term the "fast recovery," and the second we term the "slow recovery." Again, the slow recovery is not observed in shorter pulses, and the transition from "fast" to "slow" recovery is abrupt. This behavior strongly suggests that there are two phenomena involved in the transduction of analyte concentration into conductivity of a semiconducting $MoS_2$ film: one rapid and subject to saturation, and a second, slower process that integrates exposure over time. It is noted that for most nanophase chemiresistive sensors (e.g., carbon nanotubes, reduced graphene oxide, etc.), a mild thermal anneal is needed to desorb all remaining species and reach a state of total and full recovery. We have found that annealing does help with recovery in our 1T/2H devices, but the sensors return spontaneously to their initial state after a sufficiently long recovery period, which implies that these sensors could be used repeatedly without necessitating frequent cleaning.

These new sensors offer low-power, high selectivity, high sensitivity, ease of use, robustness, versatility, mechanical flexibility, and low fabrication expense characteristic. Our sensors have the potential to detect many different analytes with a single sensing suite. They are inherently nanoscale, necessitating minimal space. They require less than 1 uA of current for operation. They can operate over a much wider range of environmental conditions from cryogenic temperatures to over 600° C. and have no dependence on humidity.

Here, by incorporating phase engineering of the contacts, these new sensors are even more low-power and selective. The sensing behavior is not overwhelmed by Schottky barriers or the behavior of the contacts. These new sensors allow the intrinsic chemical vapor sensing properties of the film to dominate.

Many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

What we claim is:

1. A method of making a low dimensional material chemical vapor sensor comprising:

providing a monolayer of a transition metal dichalcogenide;

applying the monolayer of the transition metal dichalcogenide onto a $SiO_2/n^+Si$ substrate and thereby forming a device;

applying a polymethyl-methacrylate film to the monolayer of the transition metal dichalcogenide on the substrate of the device;

utilizing electron-beam lithography and defining trenches in the polymethyl-methacrylate film for the deposition of patterned metal contacts to the monolayer of a transition metal dichalcogenide and thereby creating a chemically accessible region of the transition metal dichalcogenide; and placing the device in a n-butyl lithium (nbl) bath.

2. The method of making a low dimensional material chemical vapor sensor of claim 1 wherein the n-butyl lithium (nbl) bath is a 1.6 M n-butyl lithium (nbl) bath in an argon-filled glove box.

3. The method of making a low dimensional material chemical vapor sensor of claim 1 further comprising the step of:

transitioning the accessible region of the transition metal dichalcogenide to the 1T phase while the polymethyl-methacrylate maintains coverage over remaining portions of the monolayer of the transition metal dichalcogenide maintaining the 2H phase in those regions.

4. The method of making a low dimensional material chemical vapor sensor of claim 1 wherein the monolayer of the transition metal dichalcogenide comprises $MoS_2$.

5. The method of making a low dimensional material chemical vapor sensor of claim 2 further comprising the steps of:

rinsing the device in hexane and deionized water; and depositing contacts.

6. The method of making a low dimensional material chemical vapor sensor of claim 5 wherein the contacts are Ti/Au contacts, wherein the Ti is 5 nm and wherein the Au is 35 nm.

7. The method of making a low dimensional material chemical vapor sensor of claim 6 wherein the step of depositing contacts is by electron-beam evaporation and lift-off.

8. A low dimensional material chemical vapor sensor comprising:
- a monolayer of a transition metal dichalcogenide;
- the monolayer of the transition metal dichalcogenide applied to a $SiO_2/n^+Si$ substrate;
- a region or regions of the transition metal dichalcogenide that have been treated with n-butyl lithium;
- metal contacts on the region or regions of the transition metal dichalcogenide that have been treated with the n-butyl lithium.

9. The low dimensional material chemical vapor sensor of claim 8 wherein the region or regions of the transition metal dichalcogenide that have been treated with the n-butyl lithium are transitioned to the 1T phase.

10. The low dimensional material chemical vapor sensor of claim 8 wherein the sensor spontaneously recovers after chemical exposure.

11. The low dimensional material chemical vapor sensor of claim 8 wherein the transition metal dichalcogenide is $MoS_2$.

12. The product of the process comprising:
- providing a monolayer of a transition metal dichalcogenide;
- applying the monolayer of the transition metal dichalcogenide onto a $SiO_2/n^+Si$ substrate and thereby forming a device;
- applying a polymethyl-methacrylate film to the monolayer of the transition metal dichalcogenide on the substrate of the device;
- utilizing electron-beam lithography and defining trenches in the polymethyl-methacrylate film for the deposition of patterned metal contacts to the transition metal dichalcogenide and thereby creating an accessible region of the transition metal dichalcogenide; and
- placing the device in a n-butyl lithium (nbl) bath.

* * * * *